(12) United States Patent
Nord et al.

(10) Patent No.: US 10,489,556 B2
(45) Date of Patent: Nov. 26, 2019

(54) METHOD AND APPARATUS PERTAINING TO AUTOMATED MULTI-STEP RADIATION-TREATMENT PLAN DEVELOPMENT

(71) Applicant: Varian Medical Systems International AG, Cham (CH)

(72) Inventors: Janne Nord, Espoo (FI); Juha Kauppinen, Espoo (FI); Ramin Baghaie, Espoo (FI)

(73) Assignee: Varian Medical Systems International AG, Steinhausen (CH)

( * ) Notice: Subject to any disclaimer, the term of this patent is extended or adjusted under 35 U.S.C. 154(b) by 1392 days.

(21) Appl. No.: 13/795,257

(22) Filed: Mar. 12, 2013

(65) Prior Publication Data

US 2014/0282167 A1    Sep. 18, 2014

(51) Int. Cl.
  *G06F 3/048*    (2013.01)
  *G06F 19/00*    (2018.01)

(52) U.S. Cl.
  CPC ................................. *G06F 19/3481* (2013.01)

(58) Field of Classification Search
  None
  See application file for complete search history.

(56) References Cited

U.S. PATENT DOCUMENTS

| | | | |
|---|---|---|---|
| 6,260,005 B1* | 7/2001 | Yang | A61N 5/1031 703/11 |
| 2006/0274885 A1* | 12/2006 | Wang et al. | 378/65 |
| 2007/0041497 A1* | 2/2007 | Schnarr | A61N 5/103 378/65 |
| 2007/0156453 A1* | 7/2007 | Frielinghaus | A61N 5/103 705/2 |
| 2008/0049896 A1 | 2/2008 | Kuduvalli | |
| 2009/0226060 A1* | 9/2009 | Gering | G06T 7/0081 382/128 |

* cited by examiner

*Primary Examiner* — William C Trapanese
(74) *Attorney, Agent, or Firm* — Fitch, Even, Tabin & Flannery LLP

(57) ABSTRACT

A control circuit facilitates providing a user interface to facilitate developing a radiation-treatment plan for a given patient, the user interface comprising, at least in part, an opportunity to select an automated multi-step radiation-treatment plan development capability. Upon detecting a user's selection of this automated multi-step radiation-treatment plan development capability, these teachings then provide for automatically carrying out a plurality of steps wherein at least some of the plurality of steps pertain to other than optimizing a radiation dosing. These steps are carried out without requiring further interaction with the user and yield at least one output radiation-treatment plan that is specific to the given patient and that is administrable as yielded.

21 Claims, 2 Drawing Sheets

METHOD AND APPARATUS PERTAINING TO AUTOMATED MULTI-STEP RADIATION-TREATMENT PLAN DEVELOPMENT

TECHNICAL FIELD

This invention relates generally to the development of radiation-treatment plans.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted materials and adjacent tissues, organs, or the like that are desired or even critical to continued survival of the patient. As a result, radiation is ordinarily applied in a carefully administered manner to at least attempt to restrict the radiation to a given target volume.

Radiation-treatment plans typically serve to specify any number of operating parameters as pertain to the administration of such radiation dosings with respect to a given patient. For example, many treatment plans provide for exposing the target volume to possibly varying dosages of radiation from a number of different directions.

The development of such plans typically comprises a multi-step process. This can include, for example, acquiring or otherwise accessing patient information, defining structures of interest (regarding, for example, the treatment target, adjacent organs, and so forth), creating a field setup, optimizing a treatment plan, calculating a treatment dose (or doses), evaluating and approving the plan, and scheduling the corresponding treatment. Accordingly, the development of such a plan (or plans) often comprises a lengthy process. Such temporal considerations do not always match the needs of patients, treatment planners, technicians, administrators, and other interested parties.

BRIEF DESCRIPTION OF THE DRAWINGS

The above needs are at least partially met through provision of the method and apparatus pertaining to automated multi-step radiation-treatment plan development described in the following detailed description, particularly when studied in conjunction with the drawings, wherein.

Figure 1:
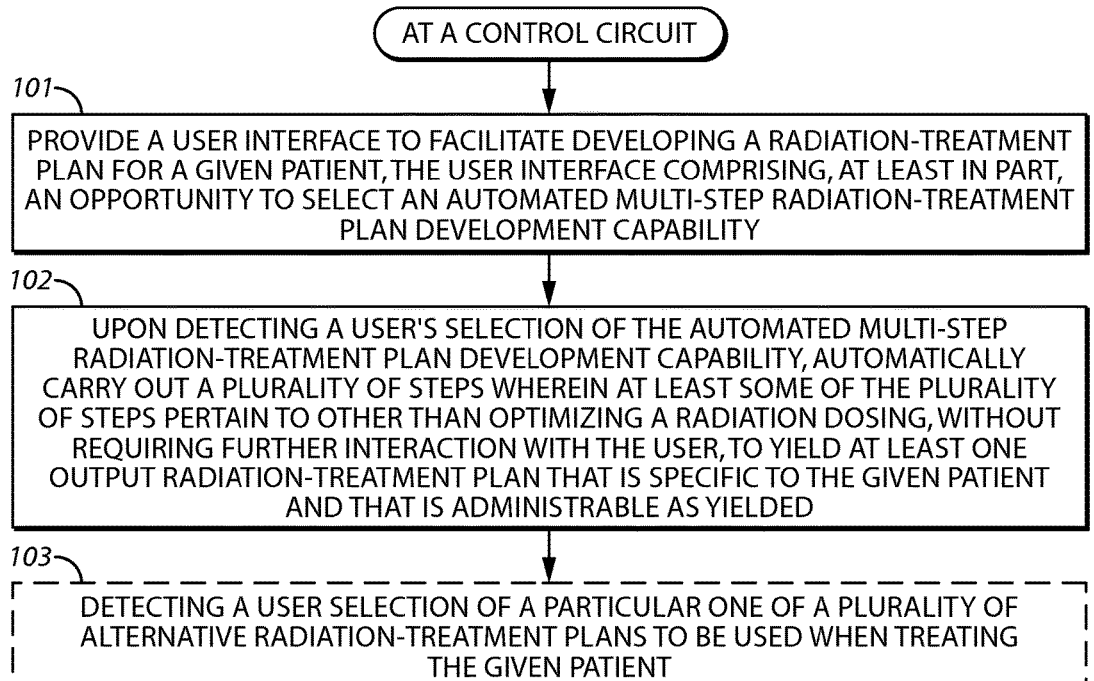
FIG. 1 comprises a flow diagram as configured in accordance with various embodiments of the invention.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, a control circuit facilitates providing a user interface to facilitate developing a radiation-treatment plan for a given patient, the user interface comprising, at least in part, an opportunity to select an automated multi-step radiation-treatment plan development capability. Upon detecting a user's selection of this automated multi-step radiation-treatment plan development capability, these teachings then provide for automatically carrying out a plurality of steps wherein at least some of the plurality of steps pertain to other than optimizing a radiation dosing. These steps are carried out without requiring further interaction with the user and yield at least one output radiation-treatment plan that is specific to the given patient and that is administrable as yielded.

The aforementioned user interface can comprise, at least in part, an active display (which may, or may not, comprise a touch screen). Other possibilities include a cursor-control component, a keyboard, and so forth.

The particular steps carried out pursuant to these teachings can vary widely with respect to the application setting. Examples include, but are not limited to, accessing physiological information regarding the given patient, processing previously-stored information regarding the given patient, comparing a plurality of candidate radiation-treatment plans to identify a recommended radiation-treatment plan to provide as the aforementioned output radiation-treatment plan, and so forth.

So configured, these teachings can facilitate, at least in some cases, more quickly or more thoroughly providing one or more radiation-treatment plans. These teachings will also accommodate the processing of such steps in a wholly or partially user-independent manner as desired. The described approaches are readily employed with a wide variety of radiation-treatment platforms, implementation parameters, planning methodologies, and so forth and hence can serve to significantly leverage the value and availability of such alternatives. These teachings are also economically practiced and are readily scaled to accommodate a wide variety of application settings.

These and other benefits may become clearer upon making a thorough review and study of the following detailed description. Referring now to the drawings, and in particular to FIG. 1, an illustrative process 100 that is compatible with many of these teachings will now be presented. This process 100 can be carried out by a control circuit of choice. Some examples in this regard appear further below.

At step 101, this process 100 provides a user interface to facilitate developing a radiation-treatment plan for a given patient. This user interface can assume different form factors and modalities as selected to suit a particular application setting. By one approach, for example, this user interface can comprise, at least in part, an active display (such as a liquid crystal display (LCD), a light-emitting diode (LED)-based display, a cathode-ray tube (CRT) display, and so forth). In such a case, this active display can further comprise, at least in part, a touch-screen display.

These teachings will also accommodate having the user interface comprise a cursor-control component (such as a mouse, a trackball, a joystick, a touchpad, and so forth) to facilitate user control of a cursor-based selector that is displayed on the active display. These teachings will further accommodate having the user interface comprise a keyboard of choice (such as, but not limited to, an alphabetic keyboard (such as a standard QWERTY keyboard)).

Such user-interface components are well known in the art. As these teachings are not overly sensitive to any particular selections in these regards, further elaboration in these regards is not presented here for the sake of brevity.

Pursuant to this step 101, this user interface includes an opportunity for an end user to select an automated multi-step radiation-treatment plan development capability. As used herein, an "opportunity" refers to a user perceptible and user-assertable mechanism by which the aforementioned capability is selected. Such an opportunity can assume many different forms depending upon the opportunities or limitations of a given application setting.

Figure 2:
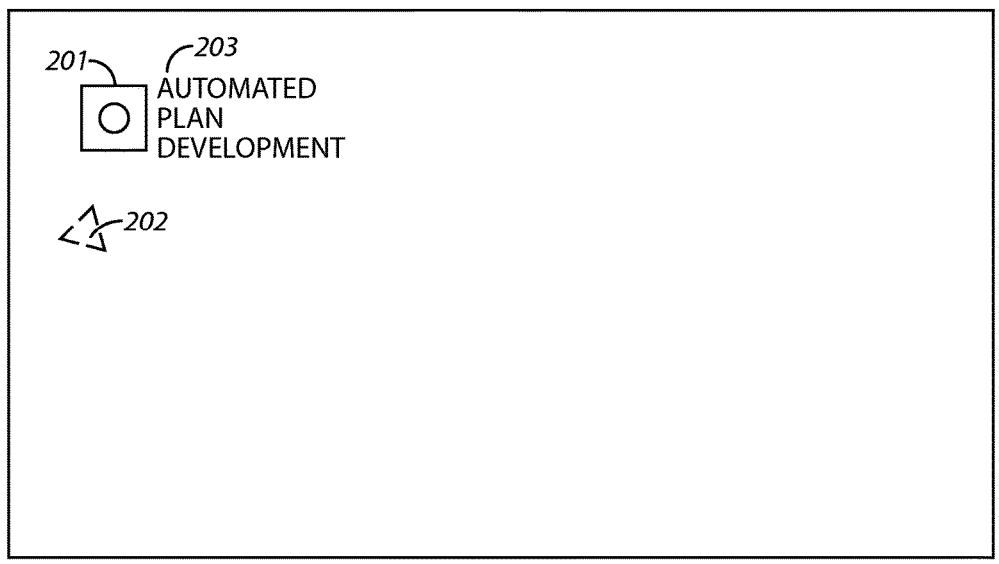
FIG. 2 comprises a schematic screen shot as configured in accordance with various embodiments of the invention.

FIG. 2 presents some illustrative but non-limiting possibilities in these regards. In this illustrative example the user interface includes, at least in part, an active display 200. The aforementioned opportunity comprises a corresponding user-selectable displayed button 201. The form factor and size of this button 201 can vary as desired. This button 201 can include corresponding explanatory or characterizing text as shown. Other graphic or iconic material can also be provided if desired to characterize the nature of the opportunity that corresponds to the button 201.

When the display 200 comprises a touch screen, the end user can select and assert this button 201 by interfacing with the display 200 using their finger (or other indicator such as a pencil or the like). When the user interface makes use of a cursor-control component, an on-screen cursor 202 can be manipulated in accordance with well-understood methodology to select and assert the button 201. And when the user interface includes a keyboard, this opportunity can be made selectable via that keyboard. For example, the "A" of the displayed expression "AUTOMATED PLAN DEVELOPMENT" can be underlined as shown to indicate that the end user can select and assert this button 201 by simultaneously asserting (for example) the "Ctrl" key on the keyboard along with the "A" key.

These teachings will accommodate the inclusion of other embellishments as desired. For example, the display 200 can display other content. This can include, for example, displays of content designed to assist the end user with conducting a non-automated multi-step radiation-treatment plan development process, displays of content specific to the given patient (such as personal identifying information, medical history, corresponding images (such as computed tomography images), and so forth), information regarding available radiation-treatment platforms, and so forth. If desired, one can also include a "help" facility to provide information to the end user regarding the nature, functionality, and operability of the automated multi-step radiation-treatment plan development process.

In any event, and referring again to FIG. 1, at step 102 this process 100 provides for detecting the end user's selection of the aforementioned automated multi-step radiation-treatment plan development capability and then responsively automatically carrying out a plurality of steps to develop one or more such radiation-treatment plans. In many application settings, this step 102 will likely follow a selection by the end user of a particular given patient for whom the plan is to be developed. By one approach at least some of these steps (and, in some cases, all of these steps) are carried out without requiring further interaction with the user.

By one approach, the one or more radiation-treatment plans yielded by this capability are specific to the given patient. This can mean, for example, that one or more of the steps takes into account information that is specific to the given patient. Examples can include, but are not limited to, medical images of the given patient, physical dimensions regarding the given patient, and so forth.

By one approach, the radiation-treatment plan (or plans) as yielded by this approach is administrable as output. Accordingly, the automatic carrying out of these steps does not simply yield some intermediary data point. Instead, the end user receives an operationally-viable radiation-treatment plan that is technically complete. A given end user may still wish to review, vet, and otherwise approve or further modify such a radiation-treatment plan, but this does not diminish the finished nature of the outputted plan.

Pursuant to one approach, at least some of these automatically carried out steps pertain to steps other than optimizing a radiation dosing. Treatment plans are often optimized prior to use (as used herein, "optimization" will be understood to refer to improving a candidate treatment plan without necessarily ensuring that the optimized result is, in fact, the singular best solution) and such optimization sometimes comprises an iterative process that automatically repeats until some concluding criterion is met. Although these teachings will accommodate including such optimization as a part of these automated steps, these teachings can also include other kinds of functionality in these regards. (When these steps do include optimizing one or more candidate radiation-treatment plans, one or more of these steps can also comprise, if desired, comparing the optimized plan (or plans) against some evaluation criteria (or against one another) to identify a recommended radiation-treatment plan to provide as the output radiation-treatment plan.) [I think that some of the features/embodiments should include 1. Allowing each user to have a pre-set customization wherein different criteria or requirements or preference can be pre-selected so that each user's automatic development would yield different plans; 2. This would also be related to using generic/knowledge or expert case plans to automatically develop a plan, and such generic case or knowledge or expert case would include contour, trajectory, segmentations, etc. that would give user a starting point that's fairly well developed or optimized to cut down time or to aid uneducated users (such as physicists or radiation oncologist in $3^{rd}$ world nations who are not as well trained as to US counterparts).]

Possible examples in these regards are many. For example, and without intending any limitations in these regards, one or more of the steps may comprise accessing physiological information regarding the given patient. Such information can comprise, for example, information regarding the location of organs and such in the patient's body along with tumors or other treatment targets. This information can also include such things as the contours and geometry of the given patient as well.

In such a case these steps can also comprise, if desired, developing at least some of this physiological information by processing previously-stored information regarding the given patient. This can comprise metrics entered by a technologist, imaging information gleaned from a computed tomography study, and so forth.

As another non-limiting example in these regards, one or more of these steps may comprise accessing operating parameter information for at least one candidate radiation-treatment platform (and possibly a plurality of such radiation-treatment platforms) and using that operating parameter information when forming a radiation-treatment plan. This can comprise information such as, for example, dosing capabilities, corresponding collimator characteristics, and so forth.

Yet other illustrative examples in these regards include, but again are not limited to, having one or more of these steps comprise:
  scheduling a radiation treatment;
  evaluating at least some automatically-generated information;
  modifying at least some automatically-generated information;
  approving at least some automatically-generated information;
  optimizing a radiation dosing;
  selecting the given patient (for example, from a list of active patients);
  selecting a patient image;
  using Standarized Uptake Value (SUV) information;
  determining a treatment method;
  modeling at least one patient support device;
  dose tracking;
  imaging the given patient;
  segmenting one or more images as correspond to the given patient; or
  determining intra-fractional motion management parameters.

The present teachings will also accommodate having at least one (but not all) of the steps comprise an administrative step. As used herein, this reference to an "administrative" step will be understood to refer to a step that directly pertains to the business aspects of administering a radiation treatment as versus, for example, technical aspects or medical aspects. Examples of administrative steps therefore include sending information to and/or receiving information from the patient's medical coverage insurance company, formulating and/or forwarding an invoice for treatment services rendered or to be rendered, updating the patient's medical records (as maintained locally and/or remotely as the case may be), and so forth.

Generally speaking, the particular steps selected and their order of implementation may, for many application settings, provide for some initial gathering of data, some assessment or pre-processing of that data to select and render that data useful for subsequent processing, some possible subsequent data gathering as possibly indicated by the foregoing activity, and the use of that data to describe a particular approach to using a particular treatment platform to treat this particular patient with radiation.

Figure 3:
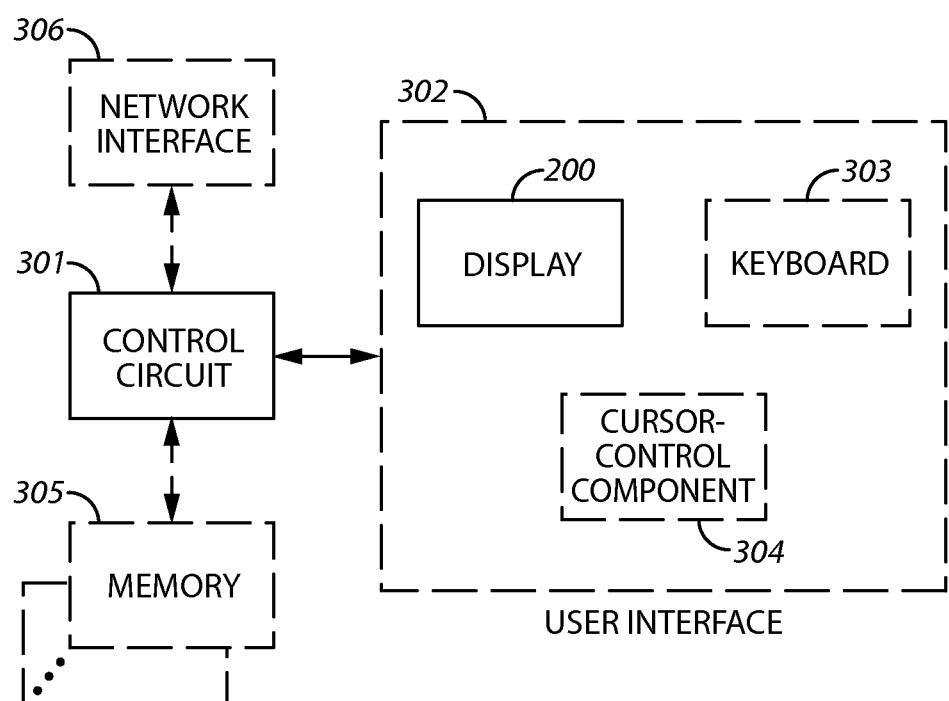
FIG. 3 comprises a block diagram as configured in accordance with various embodiments of the invention.

The above-described processes are readily enabled using any of a wide variety of available and/or readily configured platforms, including partially or wholly programmable platforms as are known in the art or dedicated purpose platforms as may be desired for some applications. Referring now to FIG. 3, an illustrative approach to such a platform 300 will now be provided.

This platform 300 comprises, in part, a control circuit 301 of choice. Such a control circuit 301 can comprise a fixed-purpose hard-wired platform or can comprise a partially or wholly programmable platform. These architectural options are well known and understood in the art and require no further description here. This control circuit 301 is configured (using, for example, corresponding programming when the control circuit 301 comprises a partially or wholly programmable platform) to carry out one or more of the steps, actions, or functions described herein.

This control circuit 301 operably couples to a user interface 302 that comprises, at least in part, a display 200 as described above. As also alluded to above, this user interface 302 can further comprise a keyboard 303, a cursor-control component 304, or both as desired. Other user-interface modalities can be accommodated as well as desired (such as, but not limited to, gesture recognition, speech recognition, and so forth).

The control circuit 301 can also optionally operably couple to one or more memories 305 if desired. Such memory 305 can serve, for example, to store patient-related data, radiation-treatment platform data, or the like that the control circuit 301 can access and utilize as per these teachings. Such memory 305 can also serve to store digital computer instructions that, when executed by the control circuit 301, cause the latter to behave as described herein.

This control circuit 301 can also optionally operably couple to one or more network interfaces 306. So configured, for example, the control circuit 301 could access remotely stored information regarding the patient or treatment platforms. As another example, one of the automatically-executed steps could comprise automatically forwarding a given candidate radiation-therapy treatment plan via an intervening network (such as the Internet) to an expert in another facility to permit the latter to approve that plan before presenting that plan to the end user of this process 100.

Such an apparatus 300 may be comprised of a plurality of physically distinct elements as is suggested by the illustration shown in FIG. 3. It is also possible, however, to view this illustration as comprising a logical view, in which case one or more of these elements can be enabled and realized via a shared platform.

So configured, one can readily facilitate the automatic multi-step formulation of one or more radiation-treatment plans. Referring again to FIG. 1, if desired, an optional step 103 can provide for detecting when an end user selects the output treatment plan (or selects a particular one of a plurality of alternative radiation-treatment plans) to be used when treating the given patient. This step might include or prompt, for example, printing the selected plan or electronically forwarding the selected plan to an implementing treatment platform. As other examples the plan could be forwarded for clinical and/or administrative approval.

As one illustrative example in these regards, an end user could select a particular patient (from amongst a plurality of displayed candidate patients, for example) and then select the aforementioned opportunity to automatically formulate a radiation-treatment plan. The particular steps then executed could be selected, by one approach, from a selection of predefined templates that define specific actions and necessary or resultant parameters. This could include, if desired, automatically detecting a default set in response to some given criterion or criteria. For example, upon automatically segmenting one or more images for the given patient, it may be automatically concluded that the image depicts a prostate. In this case, a "prostate" template could be automatically selected for use when developing a corresponding radiation-treatment plan.

Such actions could include, for example, automatically segmenting a set of structures as suggested above and then creating additional structures using Boolean operators, margin operators, or the like. A given corresponding radiation-treatment plan could then be optimized and a corresponding dose calculated. This resultant plan could then be set for evaluation. The latter might include, for example, forming and providing corresponding dose-volume histograms (DVH's), dose distribution information, and so forth.

So configured, for example, many parameter values as pertain to initially populating plan-development forms could be automatically pre-filled with default values that correspond, for example, to a particular type of identified cancer and/or identified, selected, or otherwise available treatment technique.

These teachings are highly flexible in practice and will accommodate a wide variety of radiation-treatment methodologies and platforms. These teachings are also readily scaled to accommodate as few or as many variables of interest as desired (regarding, for example, the given patient, the treatment target, the treatment platforms, and so forth). Those skilled in the art may find these teachings to be counter intuitive in that many of the steps that typically facilitate the development of a radiation-treatment plan are often viewed as requiring human judgment, consideration, input, or oversight. While small portions of such an overall process have been previously automated (such as dose calculation and structure segmentation), further automation has not been pursued. The applicant has determined, however, that for at least some application settings the approach described herein will provide an acceptable solution.

In many cases, these teachings can be expected to yield a useful result in a considerably shorter period of time than one ordinarily associates with such a task. The required time frame, for example, can be sufficiently short that the entire process, from detecting the end user's selection of the automated development capability to outputting the resultant plan (or plans), can occur while the given patient waits in a treatment position with respect to a radiation-treatment delivery platform that will implement the output radiation-treatment plan. For example, the given patient can be placed in a treatment position and then imaged (using, for example, a CT methodology of choice). These teachings could then serve to create a treatment plan based on a predefined template that is automatically filled using information gleaned from such images. (These teachings will accommodate choosing, for example, such a template (or templates) during a previous treatment session and reusing that selection for the described purposes.) More particularly, these teachings will facilitate automatically transfers structures from the new image, optimizing a treatment plan using that modified information and based, for example, on predefined objectives, and then calculate the corresponding dose and prepare the plan for evaluation. Ordinary approaches, of course, typically consume far too much time to subject a patient to such a wait or to hold the treatment platform in a quiescent mode.

Those skilled in the art will recognize that a wide variety of modifications, alterations, and combinations can be made with respect to the above described embodiments without departing from the spirit and scope of the invention.) As one example in these regards, these teachings will accommodate allowing each user to have or establish pre-set customizations wherein different criteria, requirements, or preferences are pre-selected. Such an approach would permit, for example, each user's automated multi-step radiation-treatment plan development to yield different plans that reflect those different user-specific parameters.

As another example, these teachings will also accommodate using generic knowledge and/or expert case plans to further inform the automatic development of a plan as per the foregoing. Such generic and knowledge or expert case information could include or otherwise account for such things as contouring, trajectory(ies), segmentations, and so forth. Such information could give user a starting point that is fairly well developed or even optimized to reduce processing time or to aid less experienced users.

Accordingly, it will be understood that such modifications, alterations, and combinations are to be viewed as being within the ambit of the inventive concept.

We claim:

1. A method comprising:
at a control circuit:
providing a user interface to facilitate developing a radiation-treatment plan for a given patient, the user interface comprising, at least in part, an opportunity to select an automated multi-step radiation-treatment plan development capability;
upon detecting a user's selection of the automated multi-step radiation-treatment plan development capability, automatically carrying out a plurality of steps wherein at least one of the plurality of steps comprises calculating a radiation dose to administer to the given patient and wherein:
the plurality of steps include, at least in part, comparing a plurality of candidate radiation-treatment plans to identify a recommended radiation-treatment plan to provide as the output radiation-treatment plan, wherein each of the plurality of candidate radiation-treatment plans provides for exposing a target volume in the given patient to varying doses of radiation from a number of different directions; and
some of the plurality of steps pertain to other than optimizing a radiation dosing, without requiring further interaction with the user, to yield at least one output radiation-treatment plan that is specific to the given patient and that is administrable as yielded.

2. The method of claim 1 wherein the user interface comprises, at least in part, an active display.

3. The method of claim 2 wherein the user interface comprises at least one of:
the active display comprising, at least in part, a touch-screen display;
a cursor-control component to facilitate user control of a cursor-based selector that is displayed on the active display;
a keyboard to facilitate user selection of the opportunity.

4. The method of claim 1 wherein the plurality of steps include, at least in part, accessing physiological information regarding the given patient.

5. The method of claim 4 wherein at least some of the physiological information comprises a patient image and wherein the plurality of steps include, at least in part, automatically segmenting the patient image.

6. The method of claim 1 wherein the plurality of steps include, at least in part, optimizing at least one candidate radiation-treatment plan.

7. The method of claim 1 wherein yielding at least one output radiation-treatment plan that is specific to the given patient and that is administrable as yielded comprises yielding a plurality of alternative radiation-treatment plans that are specific to the given patient and that are administrable as yielded.

8. The method of claim 7 further comprising:
detecting a user selection of a particular one of the plurality of alternative radiation-treatment plans to be used when treating the given patient.

9. The method of claim 1 wherein the plurality of steps include, at least in part, accessing operating parameter information for at least one candidate radiation-treatment platform and using that operating parameter information when forming the radiation-treatment plan.

10. The method of claim 9 wherein accessing operating parameter information for at least one candidate radiation-treatment platform comprises accessing operating parameter information for a plurality of different candidate radiation-treatment platforms and using that operating parameter information when forming the radiation-treatment plan.

11. The method of claim 1 further comprising:
detecting the user's selection of the automated multi-step radiation-treatment plan development capability while the given patient waits in a treatment position with respect to a radiation-treatment delivery platform that will implement the output radiation-treatment plan.

12. The method of claim 1 wherein at least one of the plurality of steps comprises:
scheduling a radiation treatment;
evaluating at least some automatically generated information;
approving at least some automatically generated information;
optimizing a radiation dosing;
selecting the given patient;
selecting a patient image;
using Standardized Uptake Value (SUV) information;
determining a treatment method;
modeling at least one patient support device;
dose tracking;
imaging the given patient;
determining intra-fractional motion management parameters.

13. The method of claim 12 wherein at least two of the plurality of steps comprise different ones of:
scheduling a radiation treatment;
evaluating at least some automatically generated information;
approving at least some automatically generated information;
optimizing a radiation dosing;
selecting the given patient;
selecting a patient image;
using Standardized Uptake Value (SUV) information;
determining a treatment method;
modeling at least one patient support device;
dose tracking;
imaging the given patient;
determining intra-fractional motion management parameters.

14. The method of claim 1 wherein at least one of the plurality of steps comprises an administrative step.

15. An apparatus comprising:
an active display;
a control circuit operably coupled to the active display and configured to:
provide a user interface via the active display to facilitate developing a radiation-treatment plan for a given patient, the user interface comprising, at least in part, an opportunity to select an automated multi-step radiation-treatment plan development capability;
upon detecting a user's selection of the automated multi-step radiation-treatment plan development capability, automatically carry out a plurality of steps wherein:
one of the plurality of steps comprises calculating a radiation dose to administer to the given patient;
the plurality of steps include, at least in part, comparing a plurality of candidate radiation-treatment plans to identify a recommended radiation-treatment plan to provide as the output radiation-treatment plan, wherein each of the plurality of candidate radiation-treatment plans provides for exposing a target volume in the given patient to varying doses of radiation from a number of different directions; and
wherein at least some of the plurality of steps pertain to other than optimizing a radiation dosing, without requiring further interaction with the user, to yield at least one output radiation-treatment plan that is specific to the given patient and that is administrable as yielded.

16. The apparatus of claim 15 wherein the user interface comprises at least one of:
the active display comprises, at least in part, a touch-screen display;
a cursor-control component to facilitate user control of a cursor-based selector that is displayed on the active display;
a keyboard to facilitate user selection of the opportunity.

17. The apparatus of claim 15 wherein the plurality of steps include, at least in part, accessing physiological information regarding the given patient.

18. The apparatus of claim 17 wherein the plurality of steps include, at least in part, developing at least some of the physiological information by processing previously-stored information regarding the given patient.

19. The apparatus of claim 15 wherein the plurality of steps include, at least in part, optimizing at least one candidate radiation-treatment plan.

20. The apparatus of claim 15 wherein the control circuit is configured to yield at least one output radiation-treatment plan that is specific to the given patient and that is administrable as yielded by yielding a plurality of alternative radiation-treatment plans that are specific to the given patient and that are administrable as yielded.

21. The method of claim 15 wherein the plurality of steps include, at least in part, accessing operating parameter information for at least one candidate radiation-treatment platform and using that operating parameter information when forming the radiation-treatment plan.

* * * * *

UNITED STATES PATENT AND TRADEMARK OFFICE
CERTIFICATE OF CORRECTION

PATENT NO. : 10,489,556 B2
APPLICATION NO. : 13/795257
DATED : November 26, 2019
INVENTOR(S) : Janne Nord, Juha Kauppinen and Ramin Baghaie It is certified that error appears in the above-identified patent and that said Letters Patent is hereby corrected as shown below:

In the Claims

Column 9, Line 25, in Claim 12, delete "Standarized" and insert --Standardized--.

Column 9, Line 42, in Claim 13, delete "Standarized" and insert --Standardized--.

Column 10, Line 49, in Claim 21, delete "method" and insert --apparatus--.

Signed and Sealed this
Twenty-eighth Day of January, 2020

Andrei Iancu
*Director of the United States Patent and Trademark Office*